(12) United States Patent
Jiang (10) Patent No.: US 10,980,504 B2
(45) Date of Patent: Apr. 20, 2021

(54) SYSTEMS AND METHODS FOR MOVING A COMPONENT OF AN X-RAY MACHINE

(71) Applicant: SHANGHAI UNITED IMAGING HEALTHCARE CO., LTD., Shanghai (CN)

(72) Inventor: Jinpeng Jiang, Shenzhen (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 194 days.

(21) Appl. No.: 15/965,905

(22) Filed: Apr. 28, 2018

(65) Prior Publication Data

US 2018/0303453 A1 Oct. 25, 2018

Related U.S. Application Data

(63) Continuation of application No. PCT/CN2017/120420, filed on Dec. 31, 2017.

(30) Foreign Application Priority Data

Apr. 20, 2017 (CN) .......................... 201710263261.6

(51) Int. Cl.
*H05G 1/06* (2006.01)
*A61B 6/00* (2006.01)

(52) U.S. Cl.
CPC .............. *A61B 6/548* (2013.01); *A61B 6/447* (2013.01); *A61B 6/566* (2013.01); *A61B 6/586* (2013.01); *A61B 6/44* (2013.01)

(58) Field of Classification Search
CPC .......... A61B 6/44; A61B 6/447; A61B 6/458; A61B 6/566; A61B 6/586; A61B 5/4405;
(Continued)

(56) References Cited

U.S. PATENT DOCUMENTS 2,522,147 A * 9/1950 Todd .................... A61B 6/4429
248/162.1
4,003,552 A * 1/1977 Sobolewski ........... A61B 6/105
254/283

(Continued)

FOREIGN PATENT DOCUMENTS

CN 101698463 A 4/2010
CN 201879923 U 6/2011
(Continued)

OTHER PUBLICATIONS

International Search Report for PCT/CN2017/120420 dated Mar. 29, 2018, 5 pages.
(Continued)

*Primary Examiner* — Irakli Kiknadze
(74) *Attorney, Agent, or Firm* — Metis IP LLC (57) ABSTRACT

A device may include a base, a transmission assembly, and a response assembly. The transmission assembly may be configured to move a component of a medical device. The transmission assembly may include a cable and a wheel connected to the base. An end of the cable may be connecting to a part of the component of the medical device. The response assembly may be connected to the transmission assembly. The response assembly may be configured to generate a response in response to a break of the cable.

15 Claims, 6 Drawing Sheets

(58) Field of Classification Search
CPC ... A61B 6/4233; A61B 6/4441; A61B 6/4464;
A61B 6/0407; A61B 6/0457; A61B
6/4452; A61B 6/4458; A61B 6/4476;
A61B 6/4482; A61B 6/4488; A61B
6/5211; A61B 6/5276; A61B 6/105; A61B
6/547; A61B 6/4405; A61B 6/4283; A61B
6/56; A61B 6/032; A61B 6/467; A61B
6/487; A61B 6/548; A61B 6/06; A61B
6/587; A61B 6/4411; A61B 6/54; A61B
6/542; A61B 6/08; A61B 6/4429; A61B
6/461; A61B 6/52; A61B 2017/0023;
A61B 2017/00477; A61B 2034/301;
A61B 2034/742; A61B 34/30; A61B
34/74; A61B 46/10; A61B 50/13; A61B
6/107; A61B 6/481; A61B 6/504; A61B
90/50; A61B 6/0487; A61B 6/42; A61B
6/462; A61B 6/464; A61B 2017/00809;
B66C 15/02; B66C 15/065; B66D 3/04;
B66D 1/36; H05G 1/02; G01V 1/3808;
G01V 1/3843; A61K 31/713; A61K
38/00; A61K 38/08; A61K 39/0011;
H01H 85/24; H01H 43/285; H02G 11/02;
G06T 11/005; G06T 2207/10116; G06T
17/10; G06T 2207/30036; G06T
2211/412; G06T 11/006; G06T 15/005;
G06T 2200/24; G06T 2207/10012; G06T
2207/10072; G06T 2207/10081; G06T
2207/10152; G01T 1/1647; G01T 1/17;
G01T 1/175; G01T 1/20; G01T 1/2018;
G01T 1/24; G01T 1/247; G01T 1/248;
G01T 1/2978; G01T 1/2985; G01T 7/00;
G01T 7/12; H02J 7/0021; H02J 7/0029;
H02J 7/00304; H02J 7/003; G21F 1/06;
G21F 3/00
USPC .............................. 378/62, 4, 39, 193–198
See application file for complete search history.

(56) References Cited

U.S. PATENT DOCUMENTS

| | | | |
|---|---|---|---|
| 4,807,272 A * | 2/1989 | Guenther | A61B 6/14 248/125.1 |
| 5,899,401 A | 5/1999 | Reimann et al. | |
| 6,053,255 A | 4/2000 | Crain | |
| 6,354,406 B1 * | 3/2002 | Ring | A61B 6/105 187/348 |
| 2016/0199013 A1 * | 7/2016 | Moreno Vallejo | A61B 6/4405 378/194 |
| 2018/0132809 A1 | 5/2018 | Hirata et al. | |
| 2018/0242930 A1 * | 8/2018 | Oh | A61B 6/105 |

FOREIGN PATENT DOCUMENTS

| | | |
|---|---|---|
| CN | 202043369 U | 11/2011 |
| CN | 202429825 U | 9/2012 |
| CN | 203373055 U | 1/2014 |
| CN | 103879852 A | 6/2014 |
| CN | 105384067 A | 3/2016 |
| CN | 106430025 A | 2/2017 |
| CN | 205933029 U | 2/2017 |
| CN | 106892371 A | 3/2017 |
| CN | 106725543 A | 5/2017 |
| FR | 688773 A | 8/1930 |
| JP | H03247336 A | 11/1991 |
| JP | H08157189 A | 6/1996 |

OTHER PUBLICATIONS

Written Opinion of the International Searching Authority for PCT/CN2017/120420 dated Mar. 29, 2018, 5 pages.
The Extended European Search Report in European Application No. 17906221.1 dated Mar. 31, 2020, 8 pages.
First Office Action in Chinese Application No. 201710263261.6 dated Aug. 20, 2018, 13 pages.

* cited by examiner

SYSTEMS AND METHODS FOR MOVING A COMPONENT OF AN X-RAY MACHINE

CROSS-REFERENCE TO RELATED APPLICATIONS

This application is a continuation of International Application No. PCT/CN2017/120420 filed on Dec. 31, 2017, which claims priority to Chinese Patent Application No. 201710263261.6, filed on Apr. 20, 2017. The entire contents of the above-referenced applications are hereby incorporated by reference.

TECHNICAL FIELD

The present disclosure generally relates to X-ray machines, and more specifically relates to systems and methods for moving a component of x-ray machines.

BACKGROUND

X-ray imaging is a technology that uses an X-ray scanner to scan an object to generate an X-ray image of the object. The X-ray imaging technology has been widely used in medical diagnosis, radiation therapy planning, surgery planning, and other medical procedures. In an X-ray scanner, a gantry head of the X-ray scanner may be moved based on a transmission apparatus. The transmission apparatus may include a main cable and an assistant cable. One end of the main cable may be connected to the gantry head of the X-ray scanner, and the other end of the main cable may be connected to a clump weight. One end of the assistant cable may be connected to the gantry head of the X-ray scanner, and the other end of the assistant cable may be connected to an immovable component of the X-ray scanner. When the gantry head needs to move, a user may apply a force on the gantry head. During movement of the gantry head, the main cable may undertake the weight of the gantry head. When the main cable breaks, the assistant cable may hold the gantry head to avoid the sharp drop of the gantry head. However, when the main cable breaks, a user or operator may not know the break of the main cable timely. Therefore, it is desirable to provide systems and methods for X-ray scanning to detect the break of the cable when it occurs.

SUMMARY

According to an aspect of the present disclosure, a device for transferring a component of a medical device is provided. The device may include a base, a transmission assembly, and a response assembly. The transmission assembly may be configured to move a component of a medical device. The transmission assembly may include a cable and a wheel connected to the base. An end of the cable may be connecting to a part of the component of the medical device. The response assembly may be connected to the transmission assembly. The response assembly may be configured to generate a response in response to a break of the cable.

In some embodiments, the response assembly may include a first component and a second component. The position of the first component relative to a position of the second component may change when the cable breaks.

In some embodiments, when the cable breaks, the change of the position of the first component relative to the position of the second component may include the first component coming in contact with the second component. In some embodiments, when the cable breaks, the change of the position of the first component relative to the position of the second component may include the first component becoming separated from the second component.

In some embodiments, the first component may include a rotary arm connected to the base. The rotary arm may include a first end configured to come in contact with or become separated from the second component in response to the break of the cable.

In some embodiments, the first end of the rotary arm may have a curved surface contacting with the cable.

In some embodiments, the first end of the rotary arm may include a first accessory and a second accessory. The second accessory may include a cylinder connected to the first accessory.

In some embodiments, the second accessory may include a groove configured to accommodate at least one portion of the cable.

In some embodiments, the second accessory may include a first plate and a second plate connected to the cylinder. The groove may be formed by the first plate, the second plate, and a circumference of the cylinder.

In some embodiments, the response assembly may further include a first resetting component attached to the first component. The first resetting component may be configured to cause the change of the position of the first component relative to the position of the second component when the cable breaks.

In some embodiments, the first resetting component may include at least one of an elastic part or a clump weight.

In some embodiments, the response may include generating a signal indicating the break of the cable.

In some embodiments, the response assembly may include a circuitry configured to generate the signal indicating the break of the cable.

In some embodiments, the response may include stopping the wheel to rotate.

In some embodiments, the second component may include a mechanical accessory configured to stop the wheel to rotate.

In some embodiments, the response assembly may include a first component and a second component. A position of the first component relative to a position of the second component changes when the cable breaks. In some embodiments, the mechanical part may include a support, a second resetting component, and a locking block. The support may be connected to the base. The second resetting component may be connected to the support and the locking block. The second resetting component may be configured to drive the locking block to stop the wheel in response to the change of the position of the first component relative to the position of the second component.

In some embodiments, the locking block may include a groove configured to accommodate at least one portion of the first component.

In some embodiments, the wheel may include at least one hole configured to accommodate at least one portion of the locking block.

According to an aspect of the present disclosure, a system is provided. The system may include a scanner including a radiation source and a transmission apparatus configured to transfer a component of the scanner. The transmission apparatus may include a base, a transmission assembly, and a response assembly. The transmission assembly may be configured to move a component of a medical device. The transmission assembly may include a cable and a wheel connected to the base. An end of the cable may be connecting to a part of the component of the medical device. The response assembly may be connected to the transmission assembly. The response assembly may be configured to generate a response in response to a break of the cable.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The present disclosure relates to a device and system for imaging. In some embodiments, the system may include a medical device. The medical device may include a gantry head including a radiation source and a transmission apparatus configured to transfer the gantry head. The transmission apparatus may include a base, a transmission assembly, and a response assembly. The transmission assembly may be configured to move a component of a medical device. The transmission assembly may include a cable and a wheel connected to the base. An end of the cable may be connecting to a part of the component of the medical device. The response assembly may be connected to the transmission assembly. The response assembly may be configured to generate a response in response to a break of the cable.

It should be noted that the imaging system 100 described below is merely provided for illustration purposes, and not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
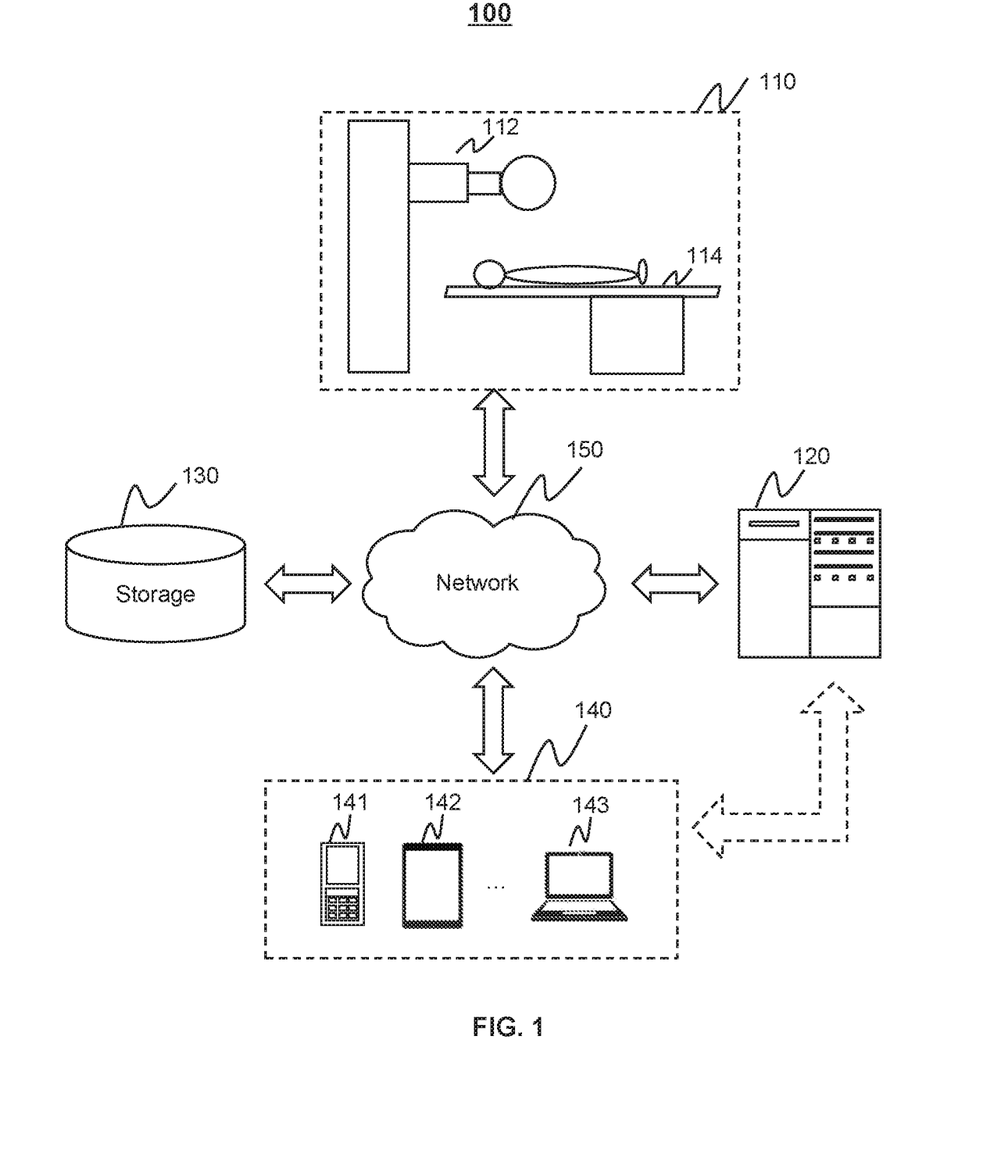
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As shown, the imaging system 100 may include an X-ray device 110, a processing device 120, a storage 130, one or more terminal(s) 140, and a network 150. In some embodiments, the X-ray device 110, the processing device 120, the storage 130, and/or the terminal(s) 140 may be connected to and/or communicate with each other via a wireless connection (e.g., the network 150), a wired connection, or a combination thereof. The connections between the components in the imaging system 100 may vary. Merely by way of example, the X-ray device 110 may be connected to the processing device 120 through the network 150, as illustrated in FIG. 1. As another example, the X-ray device 110 may be connected to the processing device 120 directly. As a further example, the storage 130 may be connected to the processing device 120 through the network 150, as illustrated in FIG. 1, or connected to the processing device 120 directly. As still a further example, the terminal(s) 140 may be connected to the processing device 120 through the network 150, as illustrated in FIG. 1, or connected to the processing device 120 directly.

The X-ray device 110 may include a gantry 112 and a table 114. The gantry 112 may include a body, a gantry head, a transmission apparatus, etc. The body may be configured to support a component of the X-ray device 110, such as the gantry head. The gantry head may include an X-ray source configured to generate and/or emit X-rays. The transmission apparatus may be configured to move the gantry head.

The processing device 120 may process data and/or information obtained from the X-ray device 110, the storage 130, and/or the terminal(s) 140. For example, the processing device 120 may reconstruct an image relating to at least one part of a subject (e.g., a tumor) based on image data collected by the X-ray device 110. As another example, the processing device 120 may determine a specific position of the gantry head of the X-ray device 110. Then, the processing device 120 may control the transmission apparatus of the X-ray device 110 to move the gantry head to the specific position. In some embodiments, the processing device 120 may be a single server or a server group. The server group may be centralized or distributed. In some embodiments, the processing device 120 may be local or remote. For example, the processing device 120 may access information and/or data from the X-ray device 110, the storage 130, and/or the terminal(s) 140 via the network 150. As another example, the processing device 120 may be directly connected to the X-ray device 110, the terminal(s) 140, and/or the storage 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof.

The storage 130 may store data, instructions, and/or any other information. In some embodiments, the storage 130 may store data obtained from the X-ray device 110, the processing device 120, and/or the terminal(s) 140. In some embodiments, the storage 130 may store data and/or instructions that the processing device 120 may execute or use to perform exemplary methods described in the present disclosure. In some embodiments, the storage 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 130 may be implemented on a cloud platform as described elsewhere in the disclosure.

In some embodiments, the storage 130 may be connected to the network 150 to communicate with one or more other components in the imaging system 100 (e.g., the processing device 120, the terminal(s) 140). One or more components in the imaging system 100 may access the data or instructions stored in the storage 130 via the network 150. In some embodiments, the storage 130 may be part of the processing device 120.

The terminal(s) 140 may be connected to and/or communicate with the X-ray device 110, the processing device 120, and/or the storage 130. For example, the terminal(s) 140 may obtain a processed image from the processing device 120. As another example, the terminal(s) 140 may obtain image data acquired via the X-ray device 110 and transmit the image data to the processing device 120 to be processed. In some embodiments, the terminal(s) 140 may include a mobile device 141, a tablet computer 142, a laptop computer 143, or the like, or any combination thereof. For example, the mobile device 140-1 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. The input information received through the input device may be transmitted to the processing device 120 via, for example, a bus, for further processing, Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120.

The network 150 may include any suitable network that can facilitate the exchange of information and/or data for the imaging system 100. In some embodiments, one or more components of the imaging system 100 (e.g., the X-ray device 110, the processing device 120, the storage 130, the terminal(s) 140, etc.) may communicate information and/or data with one or more other components of the imaging system 100 via the network 150. For example, the processing device 120 may obtain image data from the X-ray device 110 via the network 150. As another example, the processing device 120 may obtain user instruction(s) from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internee exchange points through which one or more components of the imaging system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage 130 may be a data storage including cloud computing platforms, such as public cloud, private cloud, community, and hybrid clouds, etc. However, those variations and modifications do not depart the scope of the present disclosure.

Figure 2:
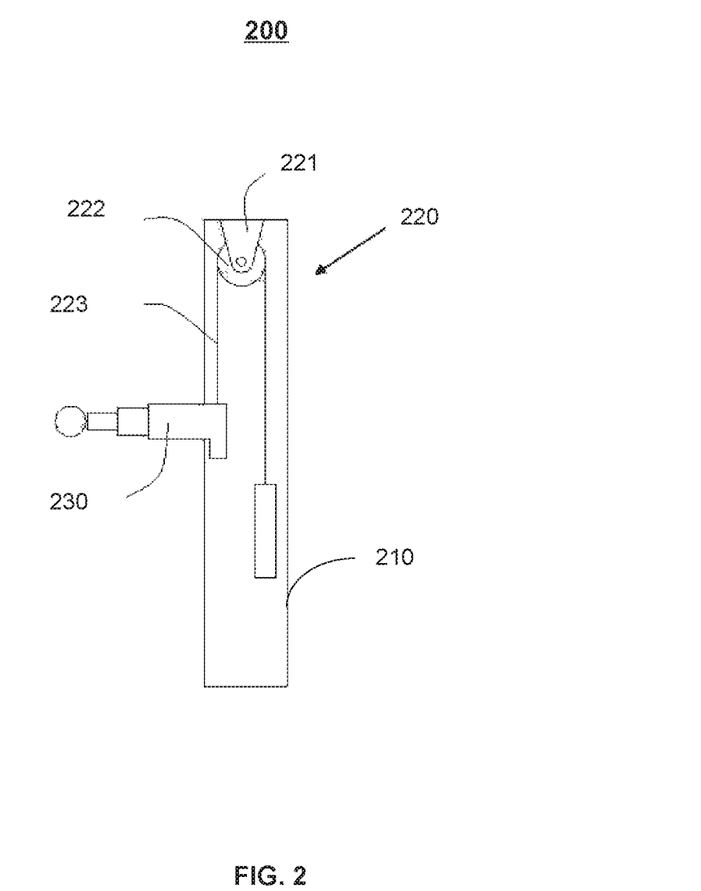
FIG. 2 illustrates a side view of an exemplary X-ray device according to some embodiments of the present disclosure.

FIG. 2 illustrates a side view of an exemplary X-ray device 200 according to some embodiments of the present disclosure. As shown in FIG. 2, the X-ray device 200 may include a body 210, a transmission apparatus 220, and a gantry head 230.

The body 210 may be configured to provide a support to a component (e.g., the transmission apparatus 220, the gantry head 230) of the X-ray device 200. The gantry head 230 may include an X-ray source. The X-ray source may generate and/or emit X-rays to scan a subject to be examined. In some embodiments, the gantry head 230 may be movable relative to the body 210. The transmission apparatus 220 may be configured to move the gantry head 230 such that the gantry head 230 may be used to scan a subject.

In some embodiments, the transmission apparatus 220 may include a base 221, a wheel 222, and a cable 223. The base 221 may be fixed to a cover of the body 210. The wheel 222 may be connected to the base 221 via, for example, a shaft. The wheel 222 may rotate relative to the shaft. In some embodiments, the wheel 222 may include a pulley. The cable 223 may pass through the wheel 222. One end of the cable 223 may be connected to the gantry head 230. The other end of the cable 223 may be connected to a clump weight. The weight of the clump weight may equal to the weight of the gantry head 230. When the gantry head 230 needs to be moved (e.g., upward or downward), a user or operator may apply a force to the gantry head 230 such that the gantry head 230 may move, for example, in a vertical direction along the rotation of the wheel 222.

In some embodiments, the transmission apparatus 220 may further include a response assembly configured to provide a response if the cable 223 breaks. In some embodiments, the response may include generating a signal indicating the break of the cable 223. The signal indicating the break of the cable 223 may be voice, an image, a text, a video, or the like, or a combination thereof. The transmission apparatus 220 may output the signal to the terminal(s) 140. Alternatively or additionally, the response may include stopping the wheel 222 to rotate. More descriptions of the transmission apparatus 220 may be found elsewhere in this disclosure (e.g., FIGS. 3-6 and the descriptions thereof).

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the X-ray device 200 may further include an assistant cable. One end of the assistant cable may be connected to the gantry head 230, and the other end of the assistant cable may be attached to an immovable component, such as the cover of the body 210. When the cable 223 breaks, the assistant cable may hold the gantry head 230 to prevent the gantry head 230 from dropping down rapidly. As another example, the transmission apparatus 220 may include a gear transmission device. The gear transmission device may include one or more gears driven by, for example, a motor. The cable 223 may include a silent chain.

Figure 3:
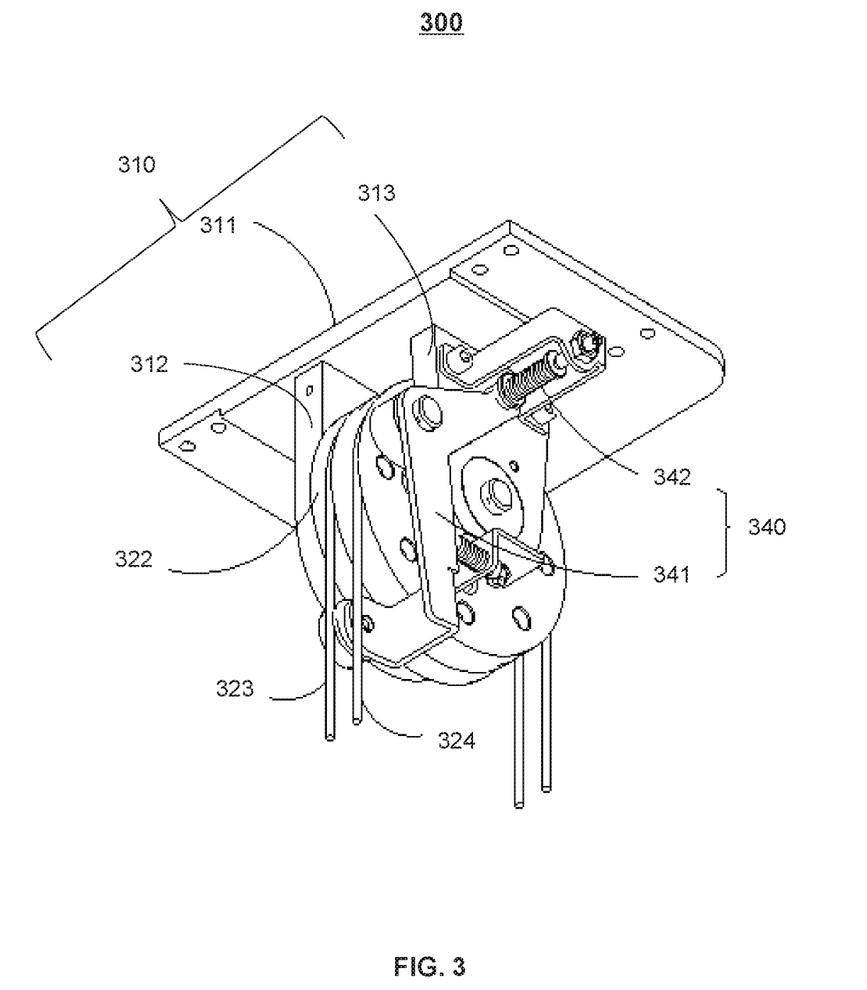
FIG. 3 is a schematic diagram of an exemplary transmission apparatus according to some embodiments of the present disclosure.

FIG. 3 is a schematic diagram of an exemplary transmission apparatus 300 according to some embodiments of the present disclosure. As shown in FIG. 3, the transmission apparatus 300 may include a base assembly 310, a wheel 322, a first cable 323, a second cable 324, and a response assembly 340. The transmission apparatus 300 may be configured to move a component of a medical device (e.g., the gantry head 230 of the X-ray device 200).

The base assembly 310 may include a substrate 311, a first lifting lug 312, and a second lifting lug 313. The substrate 311 may be coupled to an immovable component of the medical device (e.g., a cover of the body 210 of the X-ray device 200 as shown in FIG. 2). The first lifting lug 312 and the second lifting lug 313 may be mounted on the substrate 311 with a space. The space between the first lifting lug 312 and the second lifting lug 313 may be configured to accommodate the wheel 322. The wheel 322 may be connected to the first lifting lug 312 and the second lifting lug 313 respectively via a connector (not shown in FIG. 3), such as a shaft. The wheel 322 may rotate relative to the connector. The first cable 323 and the second cable 324 may pass through the wheel 322 for moving a component of a medical device (e.g., the gantry head 230 of the X-ray device 200). One end of the first cable 323 may be connected to a clump weight. The other end of the first cable 323 may be connected to the component of the medical device (e.g., the gantry head 230 of the X-ray device 200). The weight of the clump weight may be equal to that of the component of the medical device. When the component of the medical device (e.g., the gantry head 230 of the X-ray device 200) needs to move (e.g., upward or downward), a user or an operator may apply a force to the component of the medical device (e.g., the gantry head 230 of the X-ray device 200). The force applied on the component of the medical device may cause the component of the medical device (e.g., the gantry head 230 of the X-ray device 200) to move, upward or downward, along the rotation of the wheel 322. One end of the second cable 324 may be attached to an immovable component (e.g., a cover of the X-ray device 200). The other end of the second cable 324 may be connected to the component of the medical device (e.g., the gantry head 230 of the X-ray device 200). When the transmission apparatus 300 runs normally, the weight of the component of the medical device (e.g., the gantry head 230 of the X-ray device 200) may be withstood by the first cable 323. When the first cable 323 breaks, the second cable 324 may bear the weight of the component of the medical device (e.g., the gantry head 230 of the X-ray device 200). The second cable 324 may hold the component of the medical device to prevent a rapid fall of the component of the medical device (e.g., the gantry head 230 of the X-ray device 200).

The response assembly 340 may be configured to generate a response in response to a break of the first cable 323. In some embodiments, the response assembly 340 may include a first component 341 and a second component 342. The first component 341 may connect to the base assembly 310 movably. In some embodiments, the first component 341 may include a rotary arm connected to the base assembly 310. In some embodiments, the first component 341 may include a resetting component attached to the rotary arm. The resetting component may be configured to cause the first component 341 to rotate when the first cable 323 breaks. More descriptions of the first component 341 may be found elsewhere in this disclosure (e.g., FIG. 4 and the descriptions thereof). The second component 342 may be configured to generate and/or output a response in response to the break of the first cable 323. The second component 342 may be connected to the base assembly 310. In some embodiments, the second component 342 may include a circuitry configured to generate the response (e.g., a signal indicating the break of the cable). More description of the circuitry for generating the signal may be found elsewhere in this disclosure (e.g., FIG. 5 and the descriptions thereof). In some embodiments, the second component 342 may include a mechanical accessory configured to generate the response (e.g., stopping the wheel 322 to rotate). More description of the mechanical accessory for stopping the wheel 322 to rotate may be found elsewhere in this disclosure (e.g., FIG. 6 and the descriptions thereof).

In some embodiments, the position of the first component 341 relative to the position of the second component 342 may change when the first cable 323 breaks, which may trigger the second component 342 to provide the response. As used herein, the change of the position of the first component 341 relative to the second component 342 refers to that at least one portion of the first component 341 may move or rotate relative to the second component 342. For example, the change of the position of the first component 341 relative to the position of the second component 342 may include one end of the first component 341 coming in contact with at least one portion of the second component 342. As another example, the change of the position of the first component 341 relative to the position of the second component 342 may include one end of the first component 341 becoming separated from at least one portion of the second component 342.

In some embodiments, a position relationship between the first component 341 and the second component 342 may be in a first state or a second state. The first state may include the first component 341 being in contact with the second component 342. The second state may include the first component 341 being separated from the second component 342. The first state and the second state may change to another state when the first cable 323 breaks. For example, if the first component 341 is being in contact with the second component 342 before the first cable 323 breaks, the first component 341 may be separated from the second component 342 when the first cable 323 breaks. As another example, if the first component 341 is separated from the second component 342 before the first cable 323 breaks, the first component 341 may come into being in contact with the second component 342 when the first cable 323 breaks.

In some embodiments, when the transmission apparatus 300 runs normally (also referred to as the first cable 323 does not break), the first cable 323 may be in contact with the first component 341. The first cable 323 may apply a force on the first component 341 to keep the position of the first component 341 unchanged relative to the position of the second component 342. When the first cable 323 breaks, the force applied to the first component 341 by the first cable 323 may disappear. The first component 341 may be driven by the resetting component to rotate. Then, the position of the first component 341 may change relative to the position of the second component 342.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. For example, the transmission apparatus 300 may include one or more connectors and/or fixing members configured to connect the first component 341 and/or the second component 342 with the base assembly 310.

Figure 4:
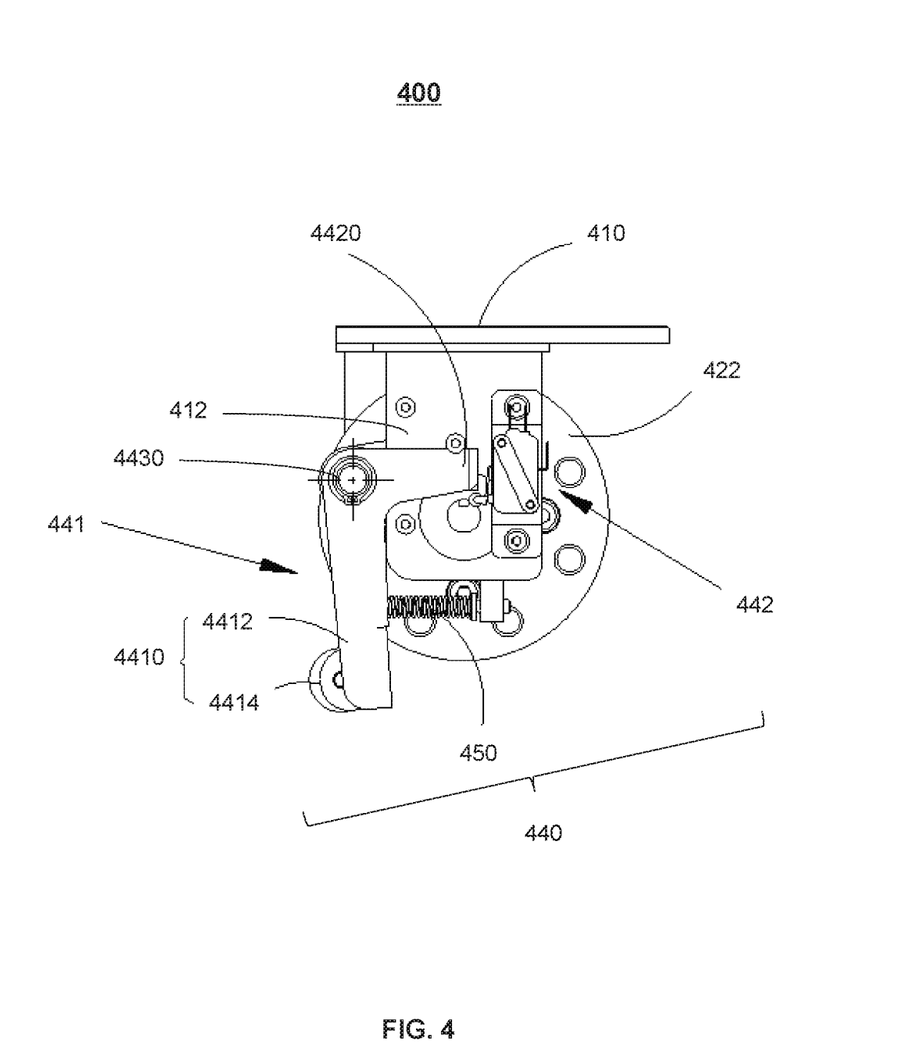
FIG. 4 is a schematic diagram of an exemplary transmission apparatus according to some embodiments of the present disclosure.

FIG. 4 is a schematic diagram of an exemplary transmission apparatus 400 according to some embodiments of the present disclosure. As illustrated in FIG. 4, the transmission apparatus 400 may include a base assembly 410, a wheel 422, and a response assembly 440. In some embodiments, the transmission apparatus 400 may further include a cable (not shown in FIG. 4) for connecting a component of a medical device (e.g., the gantry head 230 of the X-ray device 200) to a clump weight. The response assembly 440 may be configured to generate a response when the cable breaks. The response assembly 440 may include a first component 441 and a second component 442. More descriptions of the base assembly 410, the wheel 422, the first component 441, and the second component 442 may be found elsewhere in the disclosure (e.g., FIGS. 2, 3, 5, and 6, and descriptions thereof).

The first component 441 may include a rotary arm. The rotary arm may be connected to the lifting lug 412 of the base assembly 410 rotatably via a connector 4430 (e.g., a shaft). In some embodiments, the rotary arm may include a first end 4410 and a second end 4420. The connector 4430 may be disposed between the first end 4410 and the second end 4420. In some embodiments, the first end 4410 may have a curved surface contacting with the cable of the transmission apparatus 400. In some embodiments, the first end 4410 may include a first accessory 4412 and a second accessory 4414. The second accessory 4414 may be connected to the first accessory 4412. The second accessory 4414 may rotate relative to the first accessory 4412. In some embodiments, the second accessory 4414 may include a cylinder connected to the first accessory 4412. The cylinder may have a groove for accommodating at least one portion of the cable (not shown in FIG. 4) of the transmission apparatus 400. In some embodiments, the second accessory 4414 may include a first plate and a second plate connected to the cylinder. The groove may be formed by the first plate, the second plate, and a circumference of the cylinder.

In some embodiments, the transmission apparatus 400 may include a resetting component 450 associated with at least one part (e.g., the first accessory 4412 or the second accessory 4414) of the first end 4410. The resetting component 450 may be configured to cause the position of the first component 441 relative to the position of the second component 442 to change when the cable breaks. For example, when the transmission apparatus 400 runs normally (i.e., the cable does not break), the cable may be contacted with at least one part (e.g., the second accessory 4414) of the first end 4410 and apply a first force to the at least one part (e.g., the second accessory 4414) of the first end 4410. The resetting component 450 may apply a second force to the at least one part (e.g., the first accessory 4412) of the first end 4410. The first force and the second force may be equal in size and opposite in direction. The position of the first component 441 relative to the position of the second component 442 may remain unchanged under the first force and the second force. When the cable breaks, the first force applied by the cable may disappear. The second force may cause the first end 4410 to rotate. Then, the position of the first component 441 relative to a position of the second component 442 may change.

In some embodiments, the resetting component 450 may include an elastic part and/or a clump weight. For example, the resetting component may include a spring, a damper, a gum elastic, or the like, or a combination thereof. As another example, the resetting component 450 may include a clump weight connected to the second end 4420. When the cable breaks and the first force disappears, the clump weight may move downward, caused by the gravity of the clump weight. The position of the first component 441 relative to the position of the second component 442 may change. The change of the position of the first component 441 relative to the position of the second component 442 may trigger the second component 442 to provide a response as described elsewhere in this disclosure (e.g., FIGS. 3, 5, and 6, and the descriptions thereof).

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. For example, the transmission apparatus 400 may include one or more connectors and/or fixing members configured to connect the first component 441 and/or the second component 442 with the base assembly 410. As another example, the transmission apparatus 400 may also include other lifting lugs except the lifting lug 412.

In some embodiments, the first component 441 may include a sliding block. The sliding block may be connected to the lifting lug 412 moveably. The change of the position of the first component 441 relative to the position of the second component 442 may be achieved by the sliding of the sliding block relative to the lifting lug 412.

Figure 5:
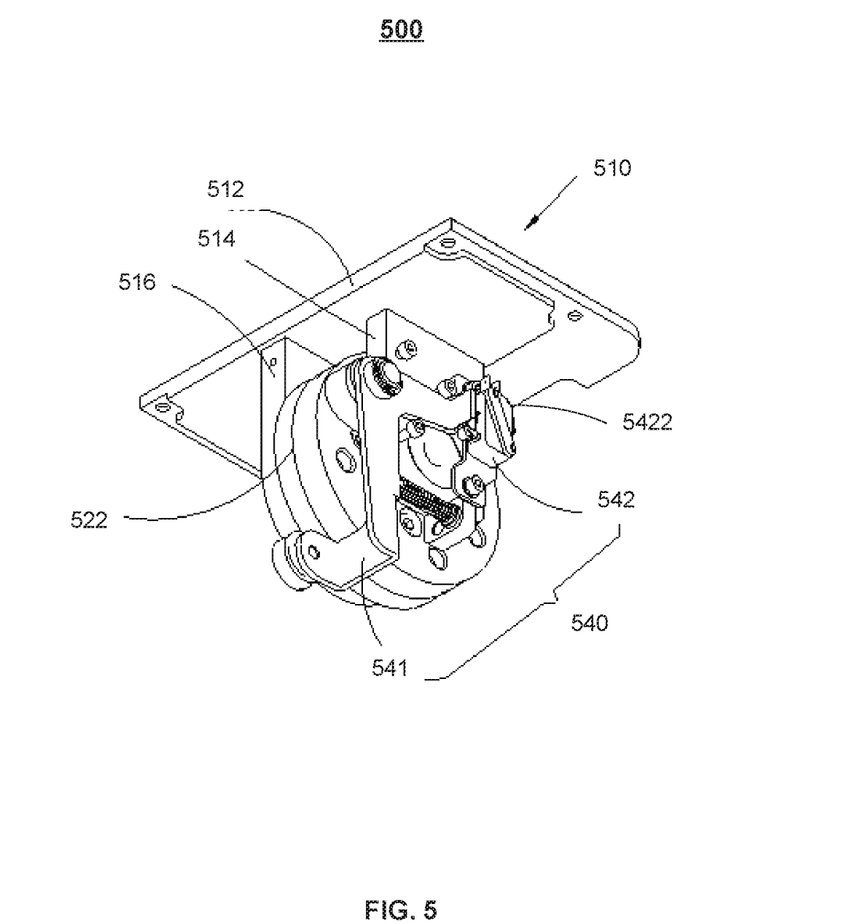
FIG. 5 is a schematic diagram of an exemplary transmission apparatus according to some embodiments of the present disclosure.

FIG. 5 is a schematic diagram of an exemplary transmission apparatus 500 according to some embodiments of the present disclosure. As illustrated in FIG. 5, the transmission apparatus 500 may include a base assembly 510, a wheel 522, and a response assembly 540. In some embodiments, the transmission apparatus 500 may further include a cable (not shown in FIG. 5) for connecting a component of a medical device (e.g., the gantry head 230 of the X-ray device 200) to a clump weight. The base assembly 510 may include a substrate 512, a first lifting lug 514, and a second lifting lug 516. The response assembly 540 may include a first component 541 and a second component 542. More descriptions of the base assembly 510, the wheel 522, the first component 541, and/or the second component 542 may be found elsewhere in the disclosure (e.g., FIGS. 2, 3, 4, and 6, and descriptions thereof).

In some embodiments, the second component 542 may include a circuitry 5422 configured to generate a signal indicating the break of the cable of the transmission apparatus 500. The signal indicating the break of the cable may be outputted by the circuitry 5422 in the form of, for example, voice, text, video, image, etc. In some embodiments, the signal indicating the break of the cable may be outputted by the circuitry 5422 to, for example, the terminal 140 to notify a user. For example, the terminal 140 may display an alert or emit a sound to notify the user of the break of the cable. For example, when the cable of the transmission apparatus 500 breaks, the first component 541 (e.g., a rotary arm) may rotate and come into contact with the second component 542, which may trigger the circuitry 5422. The circuitry 5422 may generate a sound in response to the contact between the first component 541 and the second component 542.

In some embodiments, the circuitry 5422 may include a microswitch and a processor connected to the microswitch. The microswitch may be triggered when the cable breaks to cause the circuitry 5422 to generate an electronic signal. The processor may include one or more hardware processors, such as a microcontroller, a microprocessor, a reduced instruction set computer (RISC), an application specific integrated circuits (ASICs), an application-specific instruction-set processor (ASIP), a central processing unit (CPU), a physics processing unit (PPU), a microcontroller unit, a digital signal processor (DSP), a field programmable gate array (FPGA), any circuit or processor capable of executing one or more functions, or the like, or any combinations thereof. The electronic signal may be transferred to and processed by the processor to generate a reminder indicating the break of the cable. The reminder indicating the break of the cable may be outputted by the processor to notify a user or operation the break of the cable.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. For example, the second component 542 may further include a mechanical part configured to stop the rotation of the wheel 522 when the cable breaks.

Figure 6:
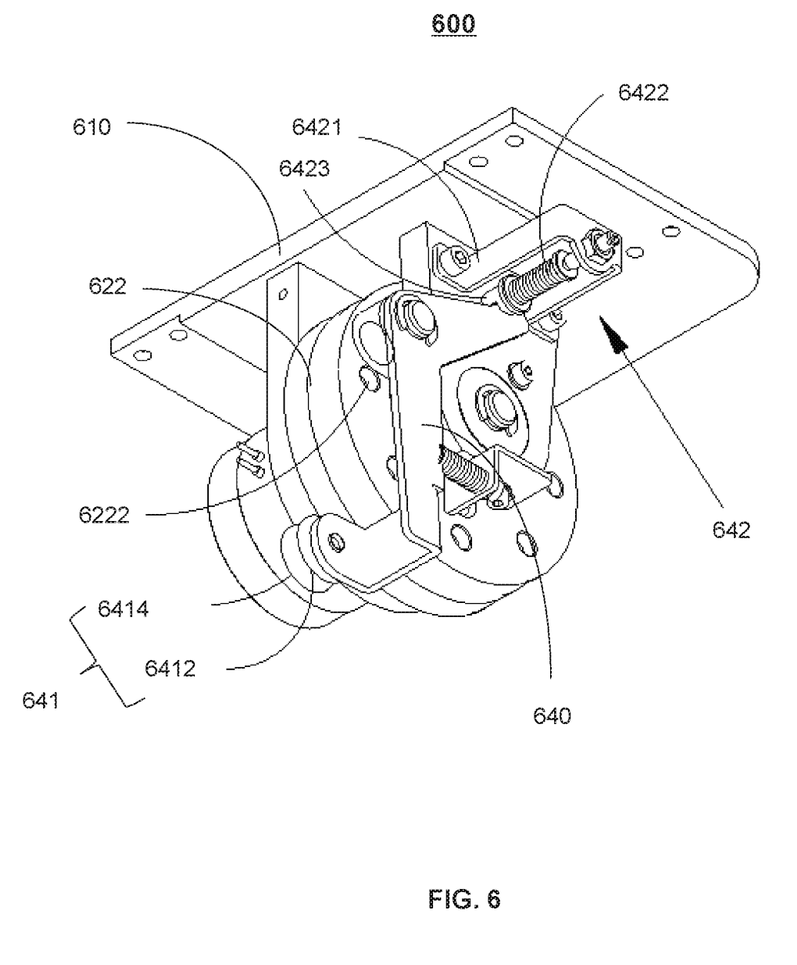
FIG. 6 is a schematic diagram of an exemplary transmission apparatus according to some embodiments of the present disclosure.

FIG. 6 is a schematic diagram of an exemplary transmission apparatus 600 according to some embodiments of the present disclosure. As illustrated in FIG. 6, the transmission apparatus 600 may include a base assembly 610, a wheel 622, and a response assembly 640. In some embodiments, the transmission apparatus 600 may further include a cable (not shown in FIG. 6) for connecting a component of a medical device (e.g., the gantry head 230 of the X-ray device 200) to a clump weight. The response assembly 640 may include a first component 641 and a second component 642. More descriptions of the base assembly 610, the wheel 622, the first component 641, and/or the second component 642 may be found elsewhere in the disclosure (e.g., FIGS. 2-5 and the descriptions thereof).

In some embodiments, the first component 641 may include a cylinder. The cylinder may include a first plate 6412 and a second plate 6414. A groove may be formed by the first plate 6412, the second plate 6414, and a circumference of the cylinder. The groove may be configured to accommodate at least one portion of the cable.

In some embodiments, the second component 642 may include a mechanical accessory configured to stop the wheel 622 from rotating. In some embodiments, the second component 642 may include a support 6421, a resetting component 6422, and a locking block 6423. The support 6421 may be fixed to the base assembly 610 (e.g., a lifting lug as described in FIG. 3). The locking block 6423 may be connected to the support 6421 movably. The resetting component 6422 may be connected with the locking block 6423 and the support 6421. When the cable of the transmission apparatus 600 breaks, the resetting component 6422 may be configured to cause the locking block 6423 to be in contact with the wheel 622, which may stop the rotation of the wheel 622. For example, when the transmission apparatus 600 runs normally (i.e., the cable does not break), one end of the first component 641 may contact to the locking block 6423 and apply a first force on the locking block 6423. The resetting component 6422 may apply a second force on the locking block 6423. The first force and the second force may be equal in size and opposite in direction. The locking block 6423 may be immobilized under the first force and the second force. When the cable breaks, the first component 641 may rotate. The end of the first component 641 may be separated from the locking block 6423. The first force may disappear, and the second force may drive the locking block 6423 to move and contact with the wheel 622, which may cause the stopping of the wheel 622.

In some embodiments, the resetting component 6422 may include an elastic part, for example, a spring, a damper, a gum elastic, or the like, or a combination thereof. In some embodiments, the locking block 6423 may have a groove. The groove on the locking block 6423 may be configured to accommodate at least one portion of the first component 641 when the transmission apparatus 600 runs normally. When the cable breaks, the at least one portion of the first component 641 may be out of the groove. The locking block 6423 may be driven by the resetting component 6422 to stop the rotation of the wheel 622. In some embodiments, the locking block 6423 may be configured with a bulge. The bulge may be configured to cooperate with the first component 641 when the transmission apparatus 600 runs normally. For example, the first component 641 may have a groove. The bulge of the locking block 6423 may be accommodated in the groove when the transmission apparatus 600 runs normally. When the cable breaks, the bulge of the locking block 6423 may be out of the groove of the first component 641. The locking block 6423 may be driven by the resetting component 6422 to stop the rotation of the wheel 622.

In some embodiments, the locking block 6423 may be configured to stop the rotation of the wheel 622 by a friction force between the locking block 6423 and the wheel 622 when the locking block 6423 is contacted with the wheel 622. In some embodiments, the wheel 622 may be configured with at least one locking hole 6222. The locking block 6423 may move toward the wheel 622 and embed in the locking hole 6222, which may stop the rotation of the wheel 622. In some embodiments, the wheel 622 may have multiple locking holes. The multiple locking holes may be arranged on the wheel 622 along the same circumference with the same or different interval. When the cable breaks, the locking block 6423 may be automatically inserted into one of the multiple locking holes closest to the locking block 6423, which may stop the wheel 622 from further rotating.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, the second component 642 may further include a circuitry described elsewhere in this disclosure (e.g., FIG. 5 and descriptions thereof). The circuitry may be configured to generate a signal indicating the break of the cable. The second component 642 may be configured to stop the rotation of the wheel 622. The signal may be output to notify the user of the break of the cable. In some embodiments, the second component 642 may include a shaft, a spring, and a wedge. The shaft may be connected to the base assembly 610. The spring may be enwrap the shaft. The spring may be coupled with the wedge. The spring and the wedge may move along the shaft. The wedge may be configured with a locking part. When the cable breaks, the first component 641 may come into contact with a surface of the wedge and slide from a small end face to the large end face. The wedge may slide along the shaft and compress the spring until the locking part locks the wheel 622.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A device for transferring a component of an X-ray medical device, comprising:
   a base;
   a transmission assembly configured to move a component of the medical device, the transmission assembly including:
      a cable, an end of the cable being connecting to a part of the component of the medical device; and
      a wheel connected to the base, wherein the cable passes through the wheel; and
   a response assembly connected to the transmission assembly, the response assembly being configured to stop the wheel from rotating in response to a break of the cable, wherein
      the response assembly includes a first component and a second component,
      the second component is configured to move and contact the wheel to stop the wheel from rotating when the cable breaks, a position of the first component relative to a position of the second component changes when the cable breaks, the change of the position of the first component relative to the position of the second component including one of: the first component coming in contact with the second component, or the first component becoming separated from the second component; and the response assembly further includes a first resetting component attached to the first component, the first resetting component being configured to, when the cable breaks, cause the change of the position of the first component relative to the position of the second component.

2. The device of claim 1, wherein the first component includes a rotary arm connected to the base, the rotary arm including a first end configured to come in contact with or become separated from the second component in response of the break of the cable.

3. The device of claim 2, wherein the first end of the rotary arm has a curved surface contacting with the cable.

4. The device of claim 3, wherein the first end of the rotary arm includes a first accessory and a second accessory, the second accessory including a cylinder connected to the first accessory.

5. The device of claim 4, wherein the second accessory includes a groove configured to accommodate at least one portion of the cable.

6. The device of claim 5, wherein
the second accessory includes a first plate and a second plate connected to the cylinder, and
the groove is formed by the first plate, the second plate, and a circumference of the cylinder.

7. The device of claim 1, wherein the first resetting component includes at least one of an elastic part or a clump weight.

8. The device of claim 1, wherein the response includes generating a signal indicating the break of the cable.

9. The device of claim 8, wherein the response assembly includes a circuitry configured to generate the signal indicating the break of the cable.

10. The device of claim 1, wherein
the second component includes a mechanical accessory configured to stop the wheel from rotating; and
the mechanical accessory includes a support, a second resetting component, and a locking block, wherein
the support is connected to the base,
the second resetting component is connected to the support and the locking block, and
the second resetting component is configured to drive the locking block to stop the wheel n response to the change of the position of the first component relative to the position of the second component.

11. The device of claim 10, wherein the locking block includes a groove configured to accommodate at least one portion of the first component.

12. The device of claim 10, wherein the wheel includes at least one hole configured to accommodate at least one portion of the locking block; and
the locking block is configured to move toward the wheel and the at least one portion of the locking block is configured to embed in the at least one hole to stop the wheel.

13. The device of claim 10, wherein
the locking block is configured to stop the wheel by a friction force between the locking block and the wheel when the locking block is contacted with the wheel.

14. A system, comprising:
a scanner including an X-ray radiation source; and
a transmission apparatus configured to transfer a component of the scanner, the transmission apparatus including;
a base;
a transmission assembly configured to move a component of the medical device, the transmission assembly including:
a cable, an end of the cable being connecting to a part of the component of the medical device; and
a wheel connected to the base, wherein the cable passes through the wheel; and
a response assembly connected to the transmission assembly, the response assembly being configured to stop the wheel from rotating in response to a break of the cable, wherein
the response assembly includes a first component and a second component,
the second component is configured to move and contact the wheel to stop the wheel from rotating when the cable breaks,
a position of the first component relative to a position of the second component changes when the cable breaks, the change of the position of the first component relative to the position of the second component including one of: the first component coming in contact with the second component, or the first component becoming separated from the second component; and
the response assembly further includes a first resetting component attached to the first component, the first resetting component being configured to, when the cable breaks, cause the change of the position of the first component relative to the position of the second component.

15. The system of claim 14, wherein the response assembly includes at least one of a circuitry configured to generate the signal indicating the break of the cable and a mechanical accessory configured to stop the wheel from rotating.

* * * * *